US00PP32095P2

(12) United States Plant Patent
Kraan

(10) Patent No.: US PP32,095 P2
(45) Date of Patent: Aug. 18, 2020

(54) ***GERANIUM* PLANT NAMED 'BOCOALSBL'**

(50) Latin Name: *Geranium wallichianum*
Varietal Denomination: Bocoalsbl

(71) Applicant: Kees Jan Kraan, Alphen aan den Rijn (NL)

(72) Inventor: Kees Jan Kraan, Alphen aan den Rijn (NL)

(73) Assignee: BOOT & CO BOOMKWEKERIJEN BV, Boskoop (NL)

( * ) Notice: Subject to any disclaimer, the term of this patent is extended or adjusted under 35 U.S.C. 154(b) by 0 days.

(21) Appl. No.: 16/602,465

(22) Filed: Oct. 10, 2019

(30) Foreign Application Priority Data

Feb. 28, 2019 (QZ) ..... PBR 2019/0566

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Geranium wallichianum* plant named 'Bocoalsbl' that is characterized by its speading/creeping plant habit that eventually forms a low mounded mat, its flowers that are light lilac blue in color with visible veins, its long blooming season; blooming from May to first frost in The Netherlands, and its sterile flowers with no seeds produced to date.

2 Drawing Sheets

Botanical classification: *Geranium wallichianum.*
Cultivar designation: 'Bocoalsbl'.

CROSS REFERENCE TO A RELATED APPLICATION

This application claims priority to European Community Plant Variety Office (CPVO) Plant Breeder's Rights Application No. 2019/0566 filed on Feb. 28, 2019, the entire contents of which is incorporated by reference herein.

BACKGROUND OF THE INVENTION

The present invention relates to a new and distinct cultivar of *Geranium* plant, botanically known as *Geranium wallichianum* 'Bocoalsbl' and will be referred to hereafter by its cultivar name, 'Bocoalsbl'. 'Bocoalsbl' is a new cultivar of herbaceous perennial grown for use as a garden plant.

'Bocoalsbl' arose from an on going breeding program conducted by the Inventor in Rijneveld, The Netherlands. The objectives of the breeding program was to develop a new cultivar of *Geranium* with a strong and healthy plant habit, a long flowering habit and unique flower color.

'Bocoalsbl' originated as a cross made by the Inventor in June of 2010 between *Geranium wallichianum* cultivars 'Crystal Lake' (U.S. Plant Pat. No. 18,982) as the female parent and 'Buxton's Variety' (not patented) as the male parent. The new *Geranium* was selected as a single unique plant in July of 2012 from amongst the resulting seedlings from the above cross.

Asexual propagation of the new cultivar was first accomplished by tissue culture using meristematic tissue under the direction of the Inventor in September of 2012 in Oude Wetering, The Netherlands. Asexual propagation by tissue culture has determined that the characteristics of the new cultivar are stable and are reproduced true to type in successive generations.

SUMMARY OF THE INVENTION

The following traits have been repeatedly observed and represent the characteristics of 'Bocoalsbl'. These attributes in combination distinguish 'Bocoalsbl' as a new and distinct cultivar of *Geranium.*

1. 'Bocoalsbl' exhibits a speading/creeping plant habit that eventually forms a low mounded mat.
2. 'Bocoalsbl' exhibits flowers that are light lilac blue in color with visible veins.
3. 'Bocoalsbl' exhibits a long blooming season; blooming from May to first frost in The Netherlands.
4. 'Bocoalsbl' exhibits sterile flowers with no seeds produced to date.

The female parent, 'Crystal Lake', differs from 'Bocoalsbl' in having flowers that are more pink in color with a silvery glow and in producing fertile seeds. The male parent, 'Buxton's Variety', differs from 'Bocoalsbl' in having flowers that are more blue in color and in producing fertile seeds. 'Bocoalsbl' can be most closely compared to the cultivars 'Gerwat' (U.S. Plant Pat. No. 12,175) and 'Noorthava' (U.S. Plant Pat. No. 25,543). 'Gerwat' is similar to 'Bocoalsbl' in having sterile flowers. 'Gerwat' differs from 'Bocoalsbl' in having a taller plant height and larger flowers that are blue and fade to violet-purple in color and have less visible veins. 'Noorthava' is similar to 'Bocoalsbl' in overall plant shape. 'Noorthava' differs from 'Bocoalsbl' in having flowers that are blue and fade to violet-blue in color and have less visible veins.

BRIEF DESCRIPTION OF THE DRAWINGS

The accompanying colored photographs illustrate the overall appearance and distinct characteristics of the new

*Geranium*. The photographs were taken of a one-year-old plant of the new cultivar as grown in a 25-cm containers (with 3 plugs/container) in Boskoop, The Netherlands.

Figure 1:
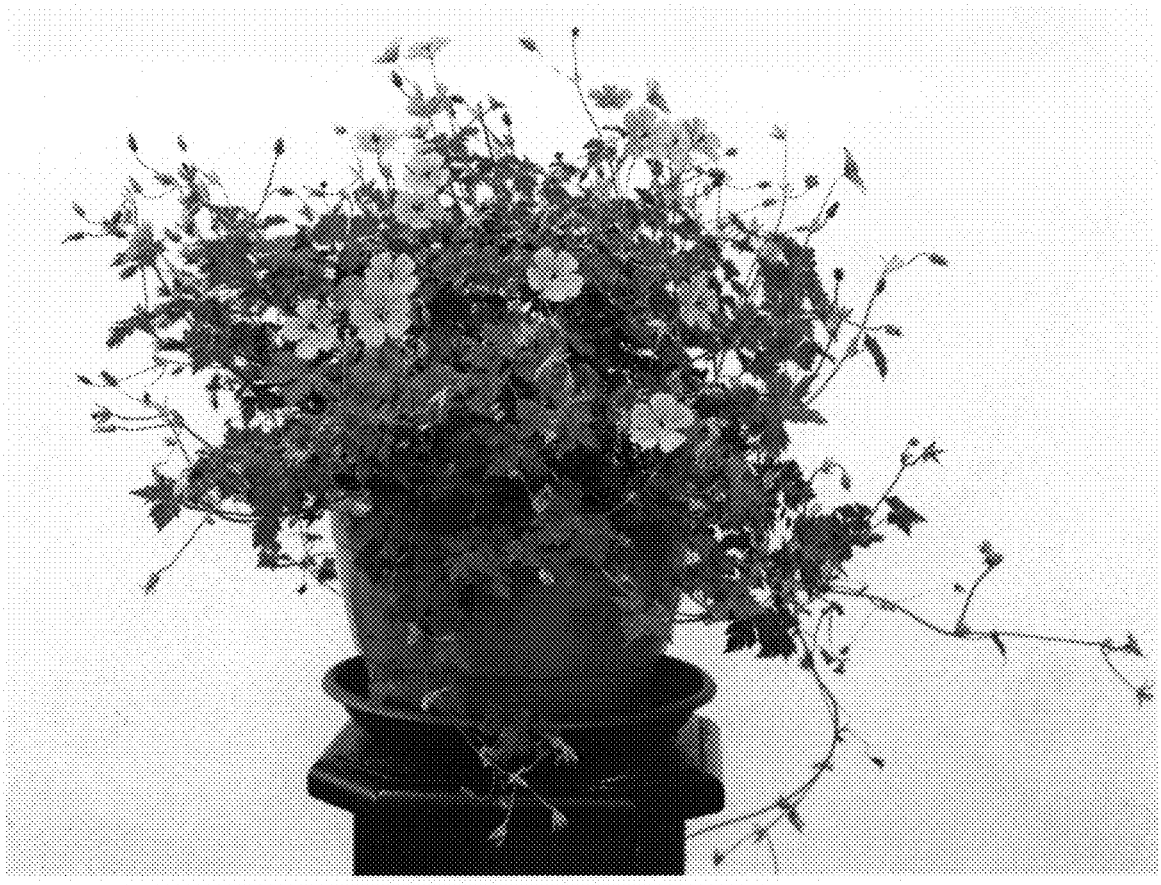

The photograph in FIG. 1 provides a side view of 'Bocoalsbl' in bloom.

Figure 2:
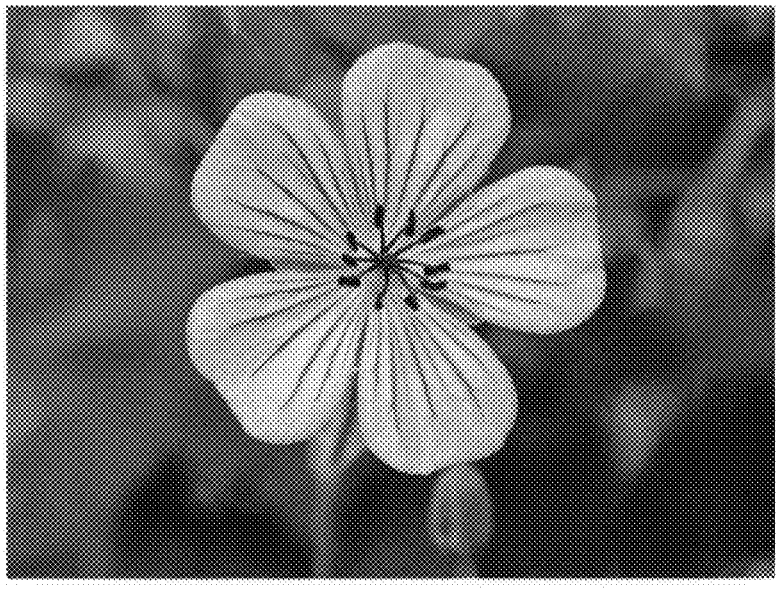

The photograph in FIG. 2 provides a close-up view of a flower of 'Bocoalsbl'.

Figure 3:
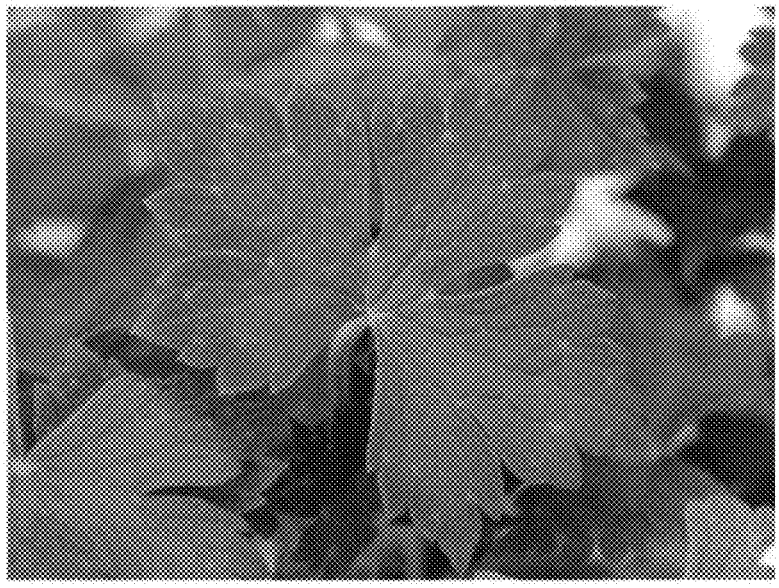

The photograph in FIG. 3 provides a close-up view of a leaf of 'Bocoalsbl'.

The colors in the photographs are as close as possible with the digital photography and printing techniques utilized and the color codes in the detailed botanical description accurately describe the colors of the new *Geranium*.

DETAILED BOTANICAL DESCRIPTION OF THE PLANT

The following is a detailed description of one-year-old plants of the new cultivar as grown in 25-cm containers (with 3 plugs/container) in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period*.—Mid-May until frost in The Netherlands.

*Plant type*.—Herbaceous perennial.

*Plant habit*.—Broadly spreading, prostrate, forming a low mounded mat in the landscape.

*Height and spread*.—Reaches average of 35 cm in height and 100 cm in spread in the landscape.

*Hardiness*.—At least in U.S.D.A. Zones 5 to 9.

*Diseases and pests*.—No susceptibility or resitance to diseases or pests has been observed.

*Root description*.—Fibrous roots extending from stout rootstock.

*Growth rate*.—Moderate to highly vigorous.

*Growth habit*.—Strong.

*Propagation*.—Tissue culture.

*Root development*.—Approximately 26 weeks to produce a young salable plant from tissue culture.

Stem description:

*Stem size*.—Average of 40.8 cm in length and 2.5 mm in width.

*Stem shape*.—Round.

*Stem strength*.—Moderately strong.

*Stem color*.—Young upper surface 144B, tinged with a color between 152A, 195A and 176A, young lower surface 144A to 144B, mature upper surface 176B, young lower surface 146D, internodes; upper surface 175A and 187B, lower surface 146D.

*Stem surface*.—Moderately glossy and sparsely covered with short hairs; an average of 1 mm in length and NN155D in color.

*Internode length*.—Average of 5.8 cm.

*Branching habit*.—Freely branched, average of 6 main branches and 14 lateral branches.

*Stem aspect*.—Held at an average angle of 65° to vertical.

Foliage description:

*Leaf shape*.—Reniform (overall shape), palmately deeply cleft with an average of five lobes.

*Leaf division*.—Simple.

*Leaf base*.—Hastate, lobes free.

*Leaf apex*.—Acute.

*Leaf venation*.—Palmate, upper surface color; 138B to 138C, lower surface color; 146D.

*Leaf margins*.—Deeply cleft with lobe margins coarsely serrate.

*Leaf aspect*.—Average of 45° to petiole.

*Leaf lobes*.—Sinuses are deep, sinus orientation is convergent.

*Leaf attachment*.—Petiolate.

*Leaf arrangement*.—Opposite.

*Leaf surface*.—Upper surface non-rugose, lower surface slightly rugose, both surfaces are matte and pubescent and covered with short hairs; an average of 0.75 mm in length and N155A in color.

*Leaf color*.—Young upper surface; 137B with small dots of 138C, young lower surface; 138A, mature upper surface; a color between 137B and 143A with small dots 138C, mature lower surface; 138B.

*Leaf size*.—Average of 4.6 cm in length and 5.5 cm in width.

*Leaf quantity*.—Average of 8 (4 pairs) per lateral branch.

*Petioles*.—Average of 5 cm in length and 1.25 mm in width, upper surface color 144B and tinged 176A to 176B, lower surface color 144B and tinged 177D, both surfaces are moderately glossy, densely covered with short hairs; an average of 0.75 mm in length and N155A, strong.

*Stipules*.—2 leafy stipules, present at the base of the leaves, broad ovate in shape, apex obtuse, trancate base, entire margins, an average of 1.3 cm in length and 9 mm in width, both surfaces 145A to 145B in color and dry to N199D.

Flower description:

*Inflorescence type*.—Single, rotate, axillary, arranged in pairs.

*Lastingness of flowers*.—About 7 days, self cleaning.

*Flower size*.—Average of 3.6 cm in diameter, 1.2 cm in depth and 3.6 cm in height.

*Flower fragrance*.—None.

*Flower number*.—Average of 240 per plant (open flowers and buds).

*Flower aspect*.—Slanted outward to upward.

*Flower type*.—Rotate.

*Flower bud size*.—An average of 1.1 cm in length, up to 5 mm in width.

*Flower bud color*.—NN137C and axially striped 143C.

*Flower bud shape*.—Ovate.

*Flower bud texture*.—Moderately covered with short hairs; an average of 1 mm in length and N155A in color.

*Petal number*.—5.

*Petal shape*.—Inverted deltoid to obcordate.

*Petal base*.—Cuneate.

*Petal apex*.—Broadly retuse.

*Petal margins*.—Entire, very slight to no undulation.

*Petal size*.—Average of 1.9 cm in length and 1.55 cm in width.

*Petal color*.—When opening upper surface; N81C, base N80D, veins darker than 77A, when opening lower surface; N81D, base N78B, veins darker than 77A, when fully open upper surface; color between N78C and N80B (closer to N80B), base N82D, veins N81A, when fully open lower surface color between 76A and N80D (closest to 76A), base NN78B, veins darker than N78A.

*Petal surface*.—Both surfaces matt, glabrous, and non-rugose with upper surface velvety and lower surface slightly velvety.

*Calyx form*.—Rotate.

*Calyx size*.—Average of 6 mm in length and 2.4 cm in width.

*Sepal number*.—Average of 5.

*Sepal shape*.—Narrow ovate.

*Sepal margin*.—Entire.

*Sepal size*.—Average of 1.4 cm length and 4 mm in width.

*Sepal surface*.—Upper surface glabrous, smooth, and moderately glossy, lower surface glabrous, smooth, and matte with main veins are densely covered with short hairs; an average of 0.75 mm in length and N155A in color.

*Sepal apex*.—Mucronate.

*Sepal base*.—Cuneate.

*Sepal color*.—When opening upper surface; 143B, margined 145B, when opening lower surface; 144A, veins 144B, when fully open upper surface; 143B, veins 145B, when fully open lower surface; 144A, veins 144B.

*Peduncle*.—Average of 5.9 cm in length and 1.55 mm in diameter, moderate to strong in strength, held at about a 35° angle relative to lateral branch, upper side 176A in color, lower side 144B in color and tinged 199A, pubescent surface; densely covered with short hairs an average of 1 mm in length and N155A in color.

*Pedicel*.—Average of 3.8 cm in length and 1 mm in diameter, moderately to strong, held at about a 30° angle relative to lateral branch, upper side 176B in color, lower side 152D in color and tinged 199C, pubescent surface; densely covered with short hairs an average of 1 mm in length and N155A in color.

*Floral bracts*.—Four bracts are placed at the top of each peduncle, elliptic in shape, slightly concave, average of 1.4 cm in length, 5 mm in width, entire margin, obtuse apex, cuneate base, upper surface smooth and glabrous, lower surface densely covered with short hairs; an average of 0.5 mm in length, N155A in color, both surfaces are 144C in color and marbeled 182B to 182C.

Reproductive organs:

*Gynoecium*.—Pistil; 1, average of 4 mm in length, stigmas; 5, decurrent, 2 mm in length, 9 mm in diameter and in between N77A and N186D in color, style; average of 2 mm in length and 143C in color, ovary; 143B in color.

*Androcoecium*.—Stamens; 10, anthers; dorsifixed, broad oblong in shape, 2 mm in length, 0.75 mm in width and 203C in color, filaments; 8 mm in length, 187A in color with base 157D, pollen is low to moderate in quantity and 202C to 202D in color.

*Fruit/seeds*.—Observed to be sterile; no fruit or seeds have been detected to date.

It is claimed:

1. A new and distinct cultivar of *Geranium* plant named 'Bocoalsbl' as herein illustrated and described.

* * * * *